(12) United States Patent
Eslami et al.

(10) Patent No.: US 9,498,120 B2
(45) Date of Patent: Nov. 22, 2016

(54) METHOD AND SYSTEM FOR OPTICAL COHERENCE ELASTOGRAPHY OF POSTERIOR PARTS OF THE EYE

(71) Applicants: Abouzar Eslami, Munich (DE); Corinna Maier-Matic, Neuried (DE); Falk Hartwig, Munich (DE); Christine Kochwagner, Rott am Inn (DE)

(72) Inventors: Abouzar Eslami, Munich (DE); Corinna Maier-Matic, Neuried (DE); Falk Hartwig, Munich (DE); Christine Kochwagner, Rott am Inn (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 14/579,678

(22) Filed: Dec. 22, 2014

(65) Prior Publication Data

US 2016/0174834 A1 Jun. 23, 2016

(51) Int. Cl.
| | |
|---|---|
| *A61B 3/10* | (2006.01) |
| *A61B 8/08* | (2006.01) |
| *A61B 3/00* | (2006.01) |
| *A61B 8/10* | (2006.01) |
| *A61B 3/12* | (2006.01) |
| *A61B 3/13* | (2006.01) |
| *A61F 9/007* | (2006.01) |
| *A61B 5/00* | (2006.01) |

(52) U.S. Cl.
CPC ............. *A61B 3/102* (2013.01); *A61B 3/0025* (2013.01); *A61B 3/0058* (2013.01); *A61B 3/12* (2013.01); *A61B 3/13* (2013.01); *A61B 5/0051* (2013.01); *A61B 8/10* (2013.01); *A61B 8/485* (2013.01); *A61F 9/00736* (2013.01)

(58) Field of Classification Search
CPC .. A61B 3/102; A61B 3/0025; A61B 3/0058; A61B 3/12; A61B 3/13; A61B 8/10; A61B 8/485; A61B 5/0051; A61F 9/00736

USPC ........ 351/206, 246; 600/318, 356, 383, 402, 600/236
See application file for complete search history.

(56) References Cited

U.S. PATENT DOCUMENTS

| | | |
|---|---|---|
| 7,359,062 B2 | 4/2008 | Chen et al. |
| 7,576,865 B2 | 8/2009 | Chen et al. |

(Continued)

FOREIGN PATENT DOCUMENTS

| | | |
|---|---|---|
| CN | 201828243 U | 5/2011 |
| WO | WO 2008/128168 | 10/2008 |

(Continued)

OTHER PUBLICATIONS

Manduca A, Oliphant TE, Dresner MA, et al, "*Magnetic Resonance Elastrography: Non-Invasive Mapping of Tissue Elasticity*", Med Image Anal 2001; 5: 237-54).

(Continued)

*Primary Examiner* — Bumsuk Won
*Assistant Examiner* — Wen Huang
(74) *Attorney, Agent, or Firm* — Patterson Thuente Pedersen, P.A.

(57) ABSTRACT

A system and method for optical coherence elastography of tissue of an eye. The method includes introducing a probe into the eye, the probe including a vibration element, generating time resolved images of the tissue of the eye located posterior the vibration element of the probe by optical coherence tomography, exciting the vibration element to ultrasonic vibrations making the tissue vibrate or oscillate, measuring a displacement of the tissue in the time resolved images, and calculating elasticity values of the tissue from the displacement.

18 Claims, 4 Drawing Sheets

(56) References Cited

U.S. PATENT DOCUMENTS

| | | |
|---|---|---|
| 8,594,757 B2 | 11/2013 | Boppart et al. |
| 2008/0228073 A1 | 9/2008 | Silverman et al. |
| 2009/0257065 A1 | 10/2009 | Hauger et al. |
| 2011/0098572 A1 | 4/2011 | Chen et al. |
| 2011/0130632 A1 | 6/2011 | McGrail et al. |
| 2012/0265061 A1 | 10/2012 | Sliwa et al. |
| 2012/0265062 A1 | 10/2012 | Sliwa et al. |
| 2013/0177274 A1 | 7/2013 | Kosenko et al. |
| 2013/0190613 A1 | 7/2013 | Boppart et al. |
| 2014/0187904 A1 | 7/2014 | Razani et al. |
| 2014/0323862 A1 | 10/2014 | Silverman et al. |
| 2015/0173605 A1* | 6/2015 | Wheatley ............... A61B 3/102 600/425 |

FOREIGN PATENT DOCUMENTS

| | | |
|---|---|---|
| WO | WO 2012/142373 | 10/2012 |
| WO | WO 2013/106285 | 7/2013 |
| WO | WO 2013/106385 | 7/2013 |

OTHER PUBLICATIONS

Schmitt J, Opt. Express, Sep. 14, 1998: 3(6): 199-211, "*OCT Elastography: Imaging Microscopic Deformation and Strain of Tissue*".

Rogowska J1, Patel NA, Fujimoto JG, Brezinski ME, Heart May 2004, 90(5): 556-62 "*Optical Coherence Tomographic Elastography Technique for Measuring Deformation and Strain of Atherosclerotic Tissues*".

Manapuram RK, Aglyamov SR, Monediado FM, Mashiatulla M, Li J Emelianiv SY, Larin KV, J. Biomed Opt, Oct. 2012, 17(10):100501, doi: 10.1117/1JB0.17.10.100501. "*In vivo Estimation of Elastic Wave Parameters Using Phase-Stabilized Swept Source Optical Coherence Elastography*".

Ford MR, Dupps WJ Jr, Rollins AM, Roy AS, Hu Z, J. Biomed Opt, Jan.-Feb. 2011: 16(1):016005, doi: 10.1117/1.3526701, "*Method for Optical Coherence Elastography of the Cornea*".

Detorakis ET, Drakonaki EE, Tsilimbaris MK, Pallikaris IG, Giarmenitis S, Ophthalmic Surg Lasers Imaging, Jan.-Feb. 2010, 41(1): 135-41, doi: 10.3928/15428877-20091230-24, "*Real-Time Ultrasound Elastographic Imaging of Ocular and Periocular Tissues: A Feasibility Study.*"

Qi W, Li R, Ma T, Li J, Kirk Shung K, Zhou Q, Chen Z., Appl Phys Lett, Sep. 2, 2013, 103(10): 103704, Epub Sep. 6, 2013, "*Resonant Acoustic Radiation Force Optical Coherence Elstography.*"

Sun C., Standish B., Yang V,X, J. Biomed Opt, Apr. 2011, 16(4): 043001, "*Optical Coherence Elastography: Current Status and Future Applications*".

Liang X, Crecea V, Boppart SA, J Innov Opt Health Sci, Oct. 2010, 3(4): 221-233, "*Dynamic Optical Coherence Elastography: A Review.*"

Zhongping C., Silverman, Rh, Qifa, Z. NIH—Research Grant. "*Elastographic Imaging of the Retina/Choroid in Age-Related Macular Degeneration.*" Dated Feb. 1, 2014.

Seimens Healthcare—"*Tissue Strain Analysis from Siemens Ultrasound.*" Website: www.healthcare.siemens.com/ultrasound/tissue-strain-analytics; 2 pgs.

\* cited by examiner

METHOD AND SYSTEM FOR OPTICAL COHERENCE ELASTOGRAPHY OF POSTERIOR PARTS OF THE EYE

FIELD OF THE INVENTION

The invention relates to ophthalmic imaging, and in particular to a method and a system for optical coherence elastography.

BACKGROUND OF THE INVENTION

The concept of elastography has been studied for more than a decade. For breast cancer, check-ups using ultrasound based technology have been developed. A further approach uses magnetic resonance imaging to obtain an elastographic imaging of tissue (cf. Manduca A, Oliphant T E, Dresner M A, et al, "Magnetic resonance elastrography: Non-invasive mapping of tissue elasticity", Med Image Anal 2001; 5: 237-54). At the microscopic level, such imaging approaches are not feasible and a finer imaging is required to detect tiny vibrations in the tissue.

The recent development of optical coherence tomography (OCT) allows fast imaging of tissue. OCT has just recently been used for elastography (cf. Schmitt J, Opt. Express, 1998 Sep. 14: 3(6):199-211, "OCT elastography: imaging microscopic deformation and strain of tissue"; and Rogowska J I, Patel N A, Fujimoto J G, Brezinski M E, Heart 2004 May, 90(5): 556-62 "Optical coherence tomographic elastography technique for measuring deformation and strain of atherosclerotic tissues"; Liang-XI, Crecea V, Boppart S A, J. Biomed Opt, 2011 Apr. 16(4):221-233, "DYNAMIC OPTICAL COHERENCE ELASTOGRAPHY: A REVIEW"). In these approaches, the tissue is excited to vibration and the mechanical response of the tissue is measured by optical coherence tomography, which has led to the term "optical coherence elastography" (OCE).

In the field of eye care, Manapuram R K, Aglyamov S R, Monediado F M, Mashiatulla M, Li J Emelianiv S Y, Larin K V, J. Biomed Opt, 2012 October 17(10):100501, doi: 10.1117/1JBO.17.10.100501, "In vivo estimation of elastic wave parameters using phase-stabilized swept source optical coherence elastography" and Ford M R I, Dupps W J Jr, Rollins A M, Roy A S, Hu Z, J. Biomed Opt, 2011 January-February: 16(1):016005, doi: 10.1117/1.3526701, "Method for optical coherence elastography of the cornea", propose to perform OCE at the cornea of the eye. The cornea is excited to mechanical vibrations by placing an ultrasonic probe directly onto the front-face of the cornea.

Detorakis E T I, Drakonaki E E, Tsilimbaris M K, Pallikaris I G, Giarmenitis S, Ophthalmic Surg Lasers Imaging, 2010 January-February, 41(1): 135-41, doi: 10.3928/15428877-20091230-24, "Real-time ultrasound elastographic imaging of ocular and periocular tissues: a feasibility study" also relate to OCE at the eye. In addition, U.S. Pat. No. 7,576,865 B1 discloses an endoscope performing OCT imaging. US 2011/0098572 A1 relates to an imaging probe for a biological sample, which probe includes an OCT probe and an ultrasound probe combined with the OCT probe in an integral probe package capable of providing by a single scanning operation images from the OCT probe and the ultrasound probe.

WO 2013/106385 A2 discloses a medical device and a method that enables determination of the elastic property of the cornea. An ultrasound probe is placed onto the front face of the cornea. The probe delivers ultrasonic energy to the cornea and measures the mechanical response of the cornea. U.S. Pat. No. 7,359,062 B2 discloses a high speed spectral domain OCT adapted for optical Doppler tomography for measuring in vivo blood flow dynamics and tissue structure.

Although the state of the art provides solutions for performing elastography of the cornea, no working solution exists for elastography of the retina. There are, however, diseases in which an elastography measurement of the retina might be of advantage. One of these diseases is the age-related macular degeneration (AMD). Under U.S. Pat. No. 8,616,071 the NIH recently granted a research grant relating to elastographic imaging of the retina in AMD, and Qi W I, Li R, Ma T, Li J, Kirk Shung K, Zhou Q, Chen Z, Appl Phys Lett, 2013 Sep. 2, 103(10): 103704, Epub 2013 Sep. 6, "Resonant acoustic radiation force optical coherence elstography", discusses the possible application of resonant acoustic radiation force as an excitation source for OCE for AMD.

Accordingly, there is a need to perform OCE at posterior parts of the eye, e.g. parts located behind the cornea or even behind the iris of the eye.

BRIEF SUMMARY OF THE INVENTION

Embodiments of the invention provide a method for optical coherence elastography of an eye. A probe is introduced into the eye at a location posterior to a cornea of the eye. The probe comprises a vibration element. Time resolved images of tissue of the eye which tissue is located posterior to the vibration element of the probe are generated by optical coherence tomography. The vibration element is excited to perform ultrasonic vibrations, which drive the tissue under examination to vibrations or oscillations. The displacement of the tissue under examination is measured in the time resolved OCT images. Elasticity values of the tissue under examination are calculated from the displacement measured.

Embodiments of the invention also provide a system for optic coherence elastography of an eye. The system comprises a probe which is adapted to be introduced into the eye. The probe comprises a vibration element. The vibration element is located at a section of the probe which is adapted to be introduced into the eye. The system further comprises a surgical microscope which images tissue under examination. The surgical microscope comprises an optical coherence tomograph which generates time resolved OCT images of the tissue of the eye. In operation, the vibration element of the system performs ultrasonic vibrations which drive the tissue under examination to vibrations or oscillations. The system further comprises a computing and controlling device which is connected to the probe and to the surgical microscope. The computing and controlling device is adapted to control the vibration element of the probe to perform the ultrasonic vibrations displacing the tissue under examination. The computing and controlling device is further adapted to read out the time resolved OCT images of the tissue under examination, and to measure a displacement of the tissue under examination in the time resolved OCT images. The computing and controlling device calculates elasticity values of the tissue under examination from the displacement measured.

In embodiments of the invention, the time resolved OCT images of the tissue under examination are sectional images of the tissue, e.g. B-scan images or 3D date cubes. In embodiments of the system, the surgical microscope generates the time resolved OCT images as time resolved sectional OCT images or time resolved OCT 3D data cubes of the tissue under examination.

In embodiments, the method further comprises determining a distance between the vibration element of the probe and the tissue, determining a force applied to the tissue on basis of the distance and at least on parameter describing the ultrasonic vibrations, and determining an original length the tissue has prior to the exititation step, wherein the displacement of the tissue is measured as a change in length of the tissue, and the elasticity values of the tissue are calculated from the force applied and a ratio of the change in length and the original length. Similar embodiments of the system comprise that the computing and controlling device determines a distance between the vibration element of the probe and the tissue, determines a force applied to the tissue on basis of the distance and at least on parameter describing the ultrasonic vibrations, determines an original length the tissue has prior to the exititation step, measures the displacement of the tissue as a change in length of the tissue, and calculates the elasticity values of the tissue from the force applied and a ratio of the change in length and the original length.

In embodiments of the present invention, the tissue is a retina of the eye, and the system images the retina. In embodiments of the method of the present invention, the time resolved images and the elasticity values are generated as a map of the retina. In embodiments of the system, the surgical microscope generates the time resolved images as a map of the retina and the computing and controlling device generates the elasticity values also as a map of the retina.

In embodiments of the invention, the probe is introduced into a vitreous humor of the eye. In embodiments of the invention, the probe is a surgical instrument, in particular a vitrectomy instrument.

In a further refinement of an embodiment, the system additionally comprises a display unit for visualizing a microscopic view overlaid by the map of elasticity values.

Embodiments of the invention measure the displacement directly from location information contained in the time resolved OCT images of the tissue under examination. Other embodiments measure the displacement of the tissue by speckle tracking in time resolved images or by cross correlation of the time resolved images with each other.

The invention can be better understood by turning to the following drawings wherein like elements are referenced by like numerals.

BRIEF DESCRIPTION OF THE DRAWINGS

The embodiments of the present invention may be more completely understood in consideration of the following detailed description of various embodiments in connection with the accompanying drawings, in which.

Figure 1:
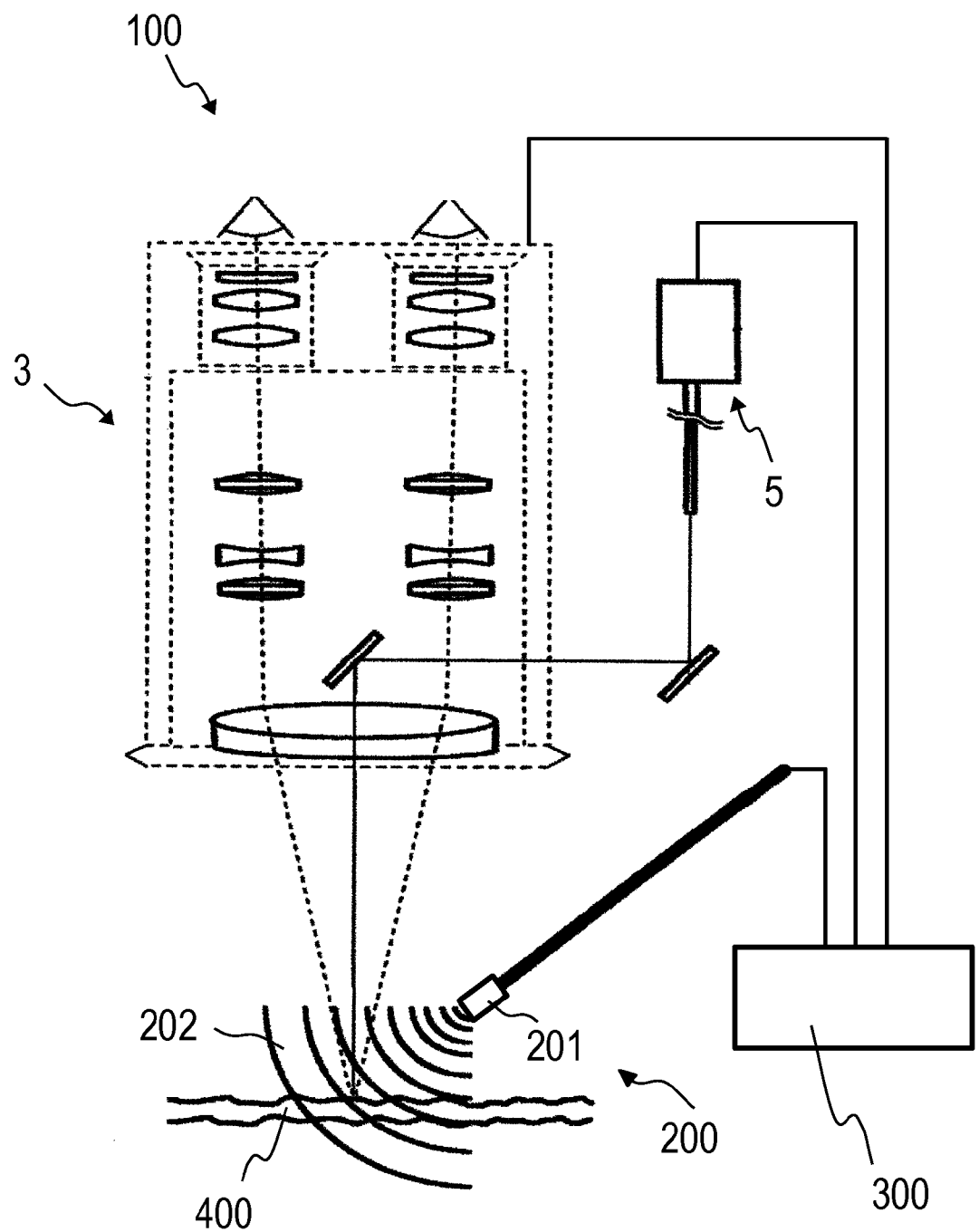
FIG. 1 is a schematic view of a system of optical coherence elastography of tissue of an eye.

While the present invention is amenable to various modifications and alternative forms, specifics thereof have been shown by way of example in the drawings and will be described in detail. It should be understood, however, that the intention is not to limit the present invention to the particular embodiments described. On the contrary, the intention is to cover all modifications, equivalents, and alternatives falling within the spirit and scope of the present invention.

DETAILED DESCRIPTION OF THE DRAWINGS

FIG. 1 shows a system for optical coherence elastography of tissue of an eye. The system comprises a surgical microscope 100, a probe 200 and a computing and controlling device 300 wherein the elements 100, 200 and 300 cooperate to perform OCE at tissue 400 of under investigation. The tissue may comprise a retina of the eye.

The surgical microscope 100 comprises an optical imaging microscope 3 and an OCT imaging device 5. The surgical microscope 100 will be explained later with reference to FIG. 3.

The system further comprises a probe 200 which comprises a vibration element 201. The vibration element 201 can be driven to ultrasonic vibrations and to emit an ultrasonic field 202. The ultrasonic field 202 excites the tissue 400 under investigation to mechanical vibrations, i.e. reciprocally displaces the tissue under investigation. The surgical microscopes generates time resolved images with its OCT imaging device. The time resolved images are OCT images. The displacement of the tissue (e.g. an amplitude of the vibrations) is measured in the time resolved images. The computing and controlling device 200 calculates elasticity values of the tissue under examination from the amplitude of the vibration.

The computing and controlling device 200 controls the probe 200 and the OCT imaging device 5 and the optical imaging microscope 3 of the surgical microscope 100. The vibration element 200 is adapted to be introduced into the eye, i.e. at a location posterior of a cornea or even an iris of the eye. This allows to locate the vibration element 201 very close to the tissue 400 under examination. The result is a strong ultrasonic field 202 at the tissue 400 generating a comparably large displacement or oscillation of the tissue. In particular, the amplitude of this displacement is significantly larger than in devices of the state of the art which couple in the ultrasonic energy from outside of the eye, e.g. by a transducer placed onto the front face of the cornea.

The stronger vibrations of the tissue gives a better resolution when calculating the elasticity values of the tissue under examination. The calculation can be done as known in the state of the art. In this respect reference is made to WO 2013/106385 A2, Ford M R I, Dupps W J Jr, Rollings A M, Roy A S, Hu Z, J. Biomed Opt, 2011 January-February, 16(1): 016005, doi: 10.1117/1.3526701, "Method for optical coherence elastography of the cornea"; Schmitt J, Opt. Express, 1998 Sep. 14; 3(6): 199-211, "OCT elastography: imaging microscopic deformation and strain of tissue"; Rogowska J I, Patel N A, Fujimoto J G, Brezinski M E, Heart, 2004 May, 90(5): 556-62, "Optical coherence tomograhic elastography technique for measing deformation and strain of atherosclerotic tissues"; Sun C I, Standish B, Yang V X, J. Biomed Opt, 2011 April, 16(4): 043001, doi: 10.1117/1.3560294, "Optical coherence elastography: current status and future applications", and Liang X I, Crecea V, Boppart S A, J Innov Opt Health Sci, 2010 October, 3(4): 221-233, "DYNAMIC OPTICAL COHERNCE ELASTOGRAPHY: A REVIEW", which all are hereby incorporated herein by reference.

The inventive system and method for optical coherence elastography of the tissue 400 uses the probe 200 which is introduced into the eye such that at least the section of the probe 200 which section comprises the vibration element 201 is within the eye. Driving the vibration element 201 into ultrasonic vibrations generates the ultrasonic field 202 and introduces external mechanical forces to the tissue 400. These mechanical forces generate a vibration of the tissue 400, which is measured by using the fast OCT imaging device 5 of the surgical microscope 100. In particular, the OCT imaging device 5 comprises a scanner to generate a 2D sectional image or a 3D data cube of the tissue 400. This will be explained later with reference to FIG. 3. Algorithms such as speckle tracking and/or cross-correlation or methods based on solving differential wave equations are then used to measure a displacement of such vibrations of the tissue 400 under examination.

Figure 2:
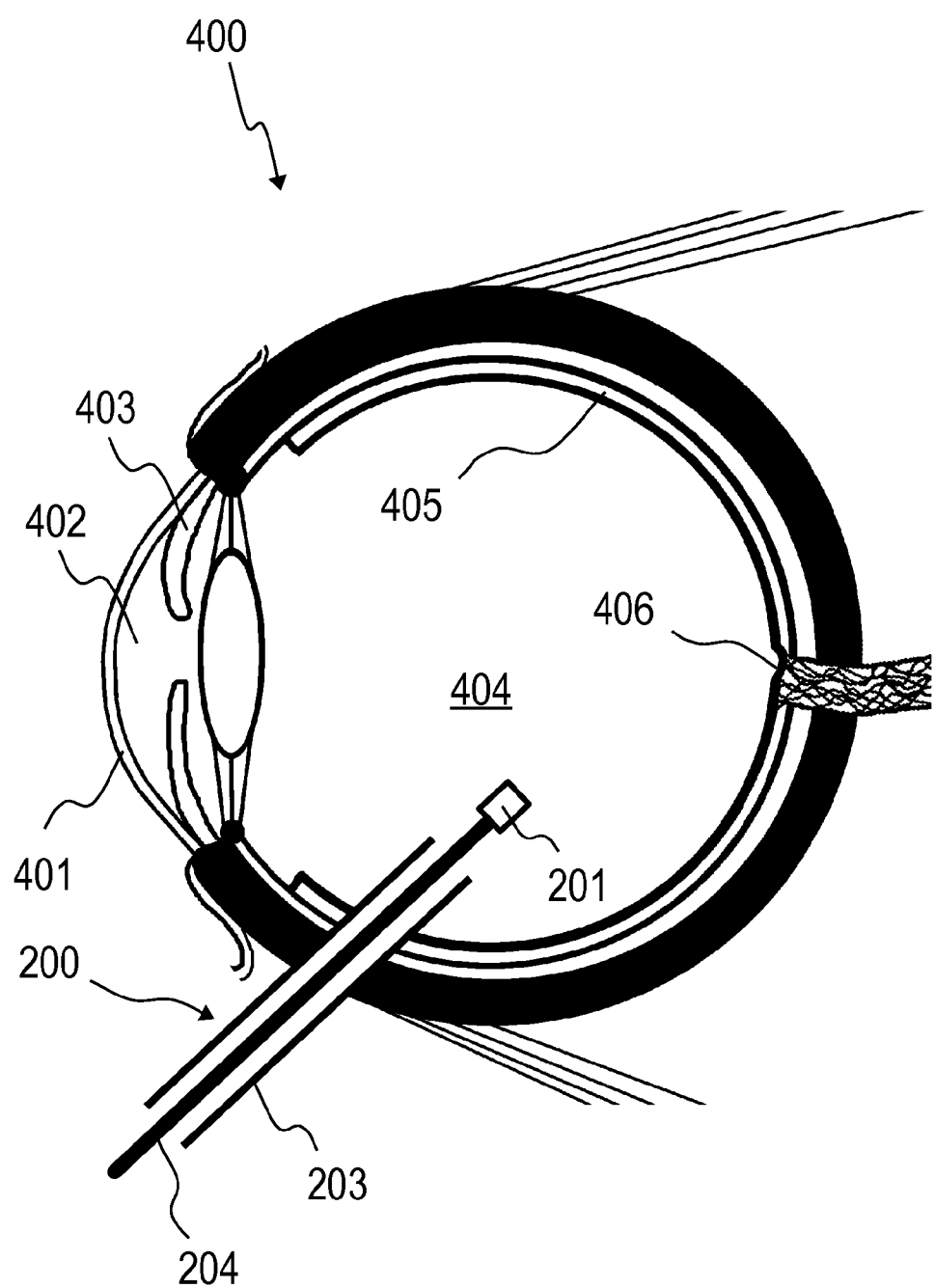
FIG. 2 shows a schematic view of the eye under examination with a probe of the system of FIG. 1 being introduced into a vitreous humor of the eye.

FIG. 2 shows an eye 400 which is to be examined by OCE. From anterior to posterior, the eye 400 comprises a cornea 401, an interior chamber 402, an iris 403, an eye lens, a vitreous humor 404 and a retina 405. The optical nerve exits from the retina 405 at an optical nerve head 406.

FIG. 2 shows the probe 200 introduced into the vitreous humor 404, with the vibration element 201 being located within the vitreous humor 404. The probe 200 comprises a trochar 203 which gives access to push a shaft 402 of the probe 200 into the eye ball and into the vitreous humor 404. The vibration element 201 is located at a distal end of the shaft 204 which is guided through the trochar 203 into the vitreous humor 404. It is clear to see that the vibration element 201 is much closer to the retina 405 and to the optical nerve head 406 than any ultrasonic transducer would be which acts from outside of the eye, e.g. is placed onto the cornea 401. In particular, the ultrasonic field generated by the vibration element 201 only has to pass the vitreous humor 404 to reach the retina 405. Contrary thereto, an ultrasonic transducer of the state of the art which would be placed onto the cornea 401 would generate an ultrasonic field that must pass the cornea 401, the interior chamber 402, the iris 403, the eye lens and then a full axial length of the vitreous humor 404 before reaching the retina 405 and in particular the optical nerve head 406. Consequently, the ultrasonic field generated by the vibration element 201 is significantly stronger and unmodified then any ultrasonic field would be which is generated for outside of the eye, e.g. from a transducer placed onto the front face of the cornea 401.

Figure 3:
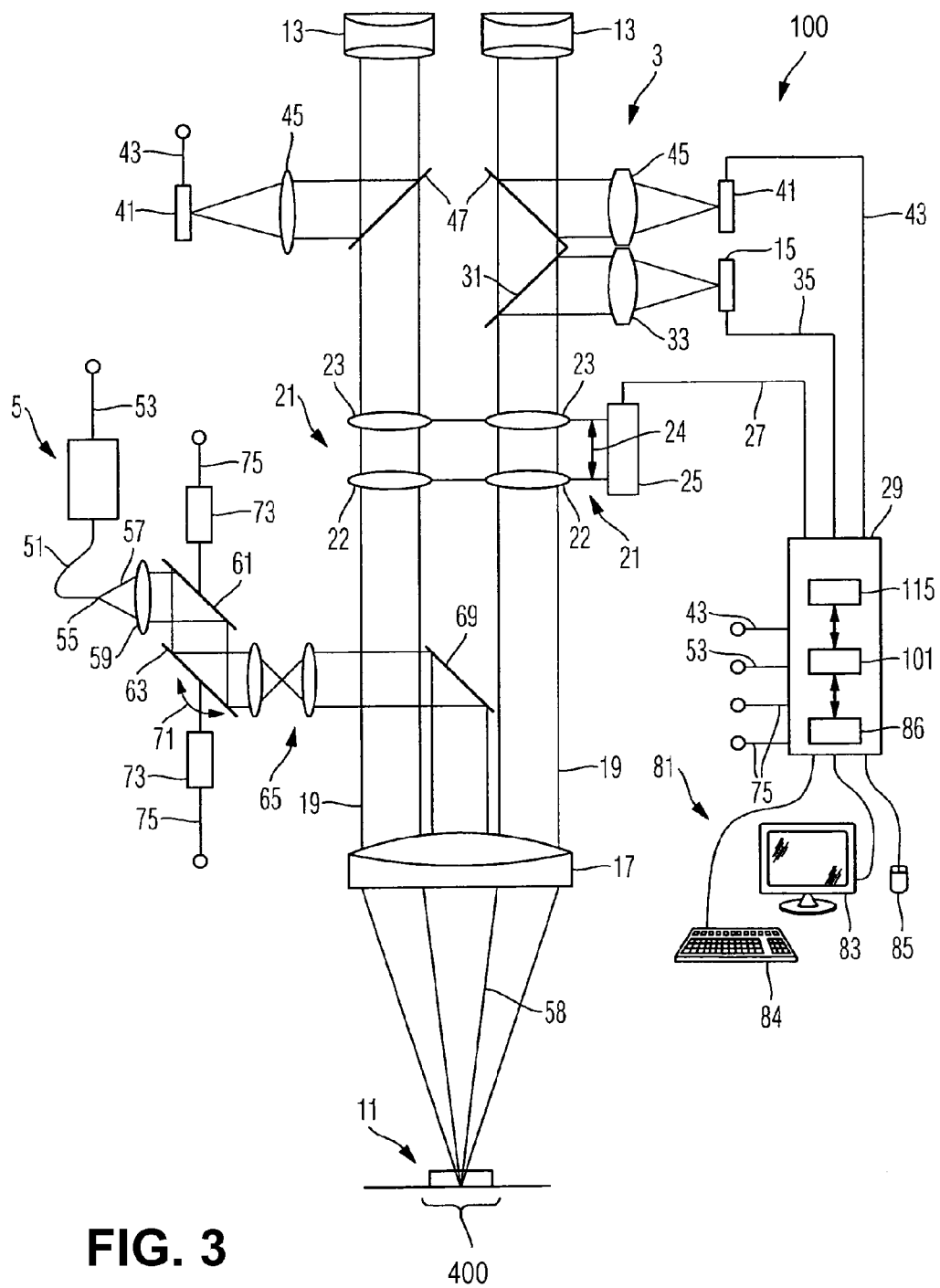
FIG. 3 is a schematic view of a surgical microscope of the system of FIG. 1.

FIG. 3 shows the surgical microscope 100 schematically. It comprises the optical imaging microscope 3 and the OCT imaging device 5. The surgical microscope is, thus, a combination or microscope. However, this is not mandatory. Some embodiments work solely with the OCT imaging devices 5, only.

The optical imaging microscope 3 images the tissue 400 located in an object field 11 to an ocular 13 and to a camera 15. The optical imaging microscope 3 comprises an objective lens 17, which can consist of one or several lens elements and which images in certain embodiments the object field 11 to infinity. In the beam path after the objective lens 17 two bundles 19 are guided through zoom lenses 21 which allow to change a magnification of the optical imaging microscope 3. The zoom lenses 21 each comprise at least two lens groups 22, 23, which can be moved in relation to each other along the main axis of the bundle 19, as FIG. 3 visualizes by an arrow 24. The lens groups 22, 23 are moved relative to each other by an actuator 25 which is controlled through a control line 27 from a control unit 29 which is part of the computing and controlling device 300.

Having been transmitted by the zoom lens 21, the beam rays 19 are guided to the ocular 13. A beam splitter 31 couples radiation from the bundle 19, which is shown on the right hand of FIG. 1 to a camera adapter 31 and onto a camera 15. The camera 15 obtains, thus, an optical image of the tissue 400. The camera 15 generates imaging data which are fed through a data line 35 to the control unit 29.

Some embodiments of the optical imaging microscope 3 comprise two electronic imaging screens 41 which obtain image data from the control unit 29 through data lines 43. The screens 41 generate images which are projected through optics 45 into the beam rays 19 by beam splitters 47. A user looking into the ocular 13 sees the images provided by the screens 41 in superposition with the image of the tissue 400.

The OCT imaging device 5 comprises a short coherent light source and an interferometer both shown only schematically in FIG. 3. Illumination radiation 57 is provided through a light conducting fiber 51 to the tissue 400. Measurement radiation reflected or backscattered at the tissue is coupled into the fiber 51.

The illumination radiation 57 exits an end S5 of the fiber 51 and is collimated by collimator optics 59 to form an OCT illumination beam 58. Two scanning mirrors 61 and 62 scan the OCT illumination beam 58. A projection optic 65 and a mirror 69 guide the scanning OCT illumination beam 58 through the objective lens 17 to the object field 11. Measurement radiation backscattered or reflected in the object field 11 are guided in the reverse direction through the objective lens 17, the projection optics 56 and collimator optics 59 and are coupled into the fiber 51.

The OCT imaging device 5 comprises the interferometer to generate time resolved OCT images either in the form of a so called B-scan or in the form of a 3D data cube. As it is known in the art, e.g. from U.S. Pat. No. 7,576,865 B1 and US 2011/0098572 A1, which are both incorporated herein by reference. The OCT imaging device 5 is connected to the control unit 29 via control and data lines 58 and transfers OCT image data over these lines to the control unit 29.

The mirrors 61, 63 are scanning mirrors to guide the OCT illumination beam 58 over the object field 11 and to collect measurement radiation from the locations in the object field 11 which are illuminated at the same time. The mirrors 81, 63 are scanning mirrors as known in the art. One Mirror 63 acts as a scanning mirror in an x direction which is the horizontal direction in FIG. 1. Arrow 71 relates to the respective movement of the mirror 63. The mirror 61 acts as a scanning mirror perpendicular to the x direction, i.e. along the y direction which is perpendicular to the drawing plane of FIG. 1. The scanning mirrors 61, 63 are driven by actuators 73 which are controlled over control lines 75 by the control unit 29. The control unit 29 can select a scanning path within the object field 11 by controlling the actuators 73.

In the embodiment shown in FIG. 3, the computing and controlling device 300 also comprises a computer 81 comprising a display 83, a keyboard 84 and a pointing device 85. A hardware or software module 86 controls the surgical microscope 100.

Figure 4:
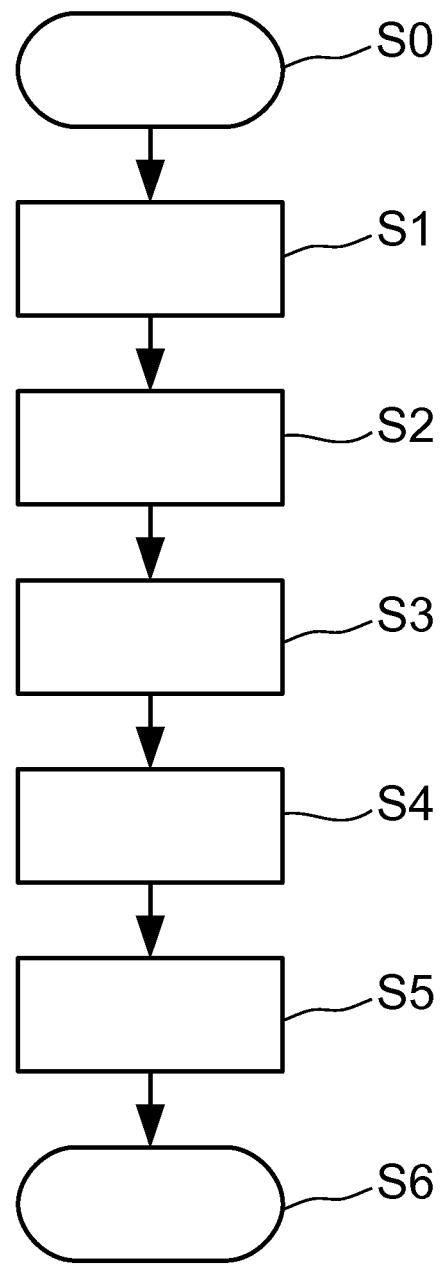
FIG. 4 is a flow diagram of a method for optical coherence elastography, which method can be performed by using the system of FIG. 1.

Referring to FIG. 4 a method for performing optical coherence elastography at the eye is explained in more detail. In some embodiments this method is performed by the system explained above. The following description explains the method with reference to the system. However, this shall not limit the invention.

In a step S0 the method is started. In a step S1, the probe 200 is inserted into the eye lens, e.g. into the vitreous humor 404 of the eye 400, such that the vibration element 201 is located within the eye.

In a step S2, the vibration element 201 is driven to ultrasonic vibrations in order to excite tissue under examination, e.g. the retina 405, to mechanical vibrations.

In a step S3, time resolved images of the tissue under examination, e.g. the retina 405 and in particular the retina around the nerve head 406, are imaged by optical coherence tomography.

In a step S4, the displacement of the tissue under investigation is measured.

A step S5 calculates elasticity values from the measured displacement. This calculation is based on the mechanical force introduced to the tissue by the ultrasonic vibrations of the vibrating element 202 of the probe 200.

The inventive system and method provide an intraoperative OCE by using OCT in combination with an ultrasonic excitation of the tissue under examination. This ultrasonic excitation generates a mechanical displacement of the tissue under examination. This mechanical displacement is strong, because the exciting element is a probe which is introduced into the eye.

The ultrasonic vibrations of the probe are known and so is, in some embodiments, also the position (e.g. by evaluating either the OCT images or the optical images) which allows to calculate elasticity values from measurements of displacement of the tissue under examination. In some embodiments, the Young's modulus is estimated from a applied force and a strain which is defined as a ratio of the change in length to an original length of the tissue under investigation. For this reason, some embodiments obtain the time resolved OCT images of the tissue under examination in a deactivated state of the vibrating element of the probe as well as in an activated state of the vibration element. OCT images obtained in the deactivated state of the vibration element gives the original length of the tissue under examination. OCT images obtained with activated vibration element allow to measure the change in length due to the mechanical excitation. Tissue elasticity can be used for tissue characterization and for distinguishing different tissues for example for segmenting an epiretinal membrane without staining or inspecting retinal detachment.

The foregoing descriptions present numerous specific details that provide a thorough understanding of various embodiments of the invention. It will be apparent to one skilled in the art that various embodiments, having been disclosed herein, may be practiced without some or all of these specific details. In other instances, components as are known to those of ordinary skill in the art have not been described in detail herein for purposes of conciseness and brevity. It is to be understood that even though numerous characteristics and advantages of various embodiments are set forth in the foregoing description, together with details of the structure and function of various embodiments, this disclosure is illustrative only and does not include all possible details and embodiments. Other embodiments may employ the principles and spirit of the present invention, and this application is expressly intended to cover any such adaptations or variations as may be suggested to one of skill in the art.

For purposes of interpreting the claims for the present invention, it is expressly intended that the provisions of 35 U.S.C. §112(f) are not to be invoked unless the specific terms "means for" or "step for" are recited in a claim.

What is claimed is:

1. A method for optical coherence elastography of a tissue of an eye, the method comprising:
   introducing at least a portion of a probe into a vitreous humor of the eye, the portion of the probe comprising a vibration element;
   generating time resolved images of the tissue of the eye, the tissue being located more posterior than the vibration element of the probe, wherein the time resolved images of the tissue are generated by optical coherence tomography;
   exciting the vibration element to ultrasonic vibrations making the tissue vibrate or oscillate;
   measuring a displacement of the tissue in the time resolved images; and
   calculating elasticity values of the tissue from the displacement.

2. The method of claim 1, wherein the time resolved images of the tissue are sectional images of the tissue.

3. The method of claim 1, further comprising:
   determining a distance between the vibration element of the probe and the tissue;
   determining a force applied to the tissue on basis of the distance and at least on parameter describing the ultrasonic vibrations; and
   determining an original length the tissue has prior to the exititation step, wherein the displacement of the tissue is measured as a change in length of the tissue, and the elasticity values of the tissue are calculated from the force applied and a ratio of the change in length and the original length.

4. The method of claim 1, wherein the tissue is a retina of the eye.

5. The method of claim 4, wherein the time resolved images and the elasticity values are generated as a map of the retina.

6. The method of claim 1, wherein the probe is a surgical instrument.

7. The method of claim 6, wherein the surgical instrument is a vitrectomy instrument.

8. The method of claim 1, wherein the displacement of the tissue is measured by speckle tracking in the time resolved images or by cross correlation of the time resolved images.

9. A system for optical coherence elastography of a tissue of an eye, the system comprising:
   a probe adapted to be introduced at least partially into the eye at a location posterior to the iris, the probe comprising a vibration element adapted to be located in a vitreous humor of the eye;
   a surgical microscope imaging the tissue and comprising an optical coherence tomograph generating time resolved images of the tissue of the eye the tissue being located more posterior than the vibration element of the probe, wherein time resolved images are generated by optical coherence tomography; and
   a computing and controlling device connected to the probe and to the surgical microscope and which device is adapted to control the vibration element to perform ultrasonic vibrations making the tissue vibrate or oscillate, to measure a displacement of the tissue in the time resolved images, and to calculate elasticity values of the tissue from the displacement.

10. The system of claim 9, wherein the tissue is a retina of the eye and the surgical microscope comprises a retina motion compensation and stabilization unit.

11. The system of claim 9, wherein surgical microscope generates the time resolved images as time resolved sectional images of the tissue.

12. The system of claim 9, wherein the computing and controlling device determines a distance between the vibration element of the probe and the tissue, determines a force applied to the tissue on basis of the distance and at least one parameter describing the ultrasonic vibrations, determines an original length the tissue has prior to excitation, measures the displacement of the tissue as a change in length of the tissue, and calculates the elasticity values of the tissue from the force applied and a ratio of the change in length and the original length.

13. The system of claim 9, wherein the surgical microscope images a retina of the eye.

14. The system of claim 13, wherein the surgical microscope generates the time resolved images as a map of the retina and wherein the computing and controlling device generates the elasticity values as a map of the retina.

15. The system of claim 14, further comprising a display unit for visualizing a microscopic view overlaid by the elasticity values.

16. The system of claim 9, wherein the probe is a surgical instrument.

17. The system of claim 16, wherein the surgical instrument is a vitrectomy instrument.

18. The system of claim 9, wherein the computing and controlling device measures the displacement of the tissue by speckle tracking in the time resolved images or by cross correlation of the time resolved images.

* * * * *